(12) United States Patent
Massironi

(10) Patent No.: US 7,727,551 B2
(45) Date of Patent: Jun. 1, 2010

(54) ORAL PHARMACEUTICAL COMPOSITIONS WITH MODIFIED RELEASE OF THE ACTIVE INGREDIENT

(75) Inventor: Maria Gabriella Massironi, London (GB)

(73) Assignee: Farmatron Ltd., London (GB)

( * ) Notice: Subject to any disclaimer, the term of this patent is extended or adjusted under 35 U.S.C. 154(b) by 1611 days.

(21) Appl. No.: 10/482,461

(22) PCT Filed: Jun. 19, 2002

(86) PCT No.: PCT/EP02/06749

§ 371 (c)(1), (2), (4) Date: Jun. 17, 2004

(87) PCT Pub. No.: WO03/002151

PCT Pub. Date: Jan. 9, 2003

(65) Prior Publication Data

US 2004/0213844 A1    Oct. 28, 2004

(30) Foreign Application Priority Data

Jun. 26, 2001    (IT)    .......................... MI2001A1337

(51) Int. Cl.
*A61K 9/14*    (2006.01)
(52) U.S. Cl. ...................................... 424/486; 424/484
(58) Field of Classification Search ....................... None
See application file for complete search history.

(56) References Cited

U.S. PATENT DOCUMENTS 6,248,363 B1 *    6/2001    Patel et al. .................. 424/497

FOREIGN PATENT DOCUMENTS

| EP | 0 514 008 A | 11/1992 |
|---|---|---|
| WO | WO 00/76478 A | 12/2000 |

* cited by examiner

*Primary Examiner*—Humera N Sheikh
(74) *Attorney, Agent, or Firm*—Porzio, Bromberg & Newman, P.C.

(57) ABSTRACT

The present invention relates to modified-release oral pharmaceutical compositions containing one or more active principles solubilized, suspended or embedded in a suitably formulated amphiphilicmatrix which, loaded in hydrophilic matrices, provides different release profiles.

9 Claims, No Drawings

ORAL PHARMACEUTICAL COMPOSITIONS WITH MODIFIED RELEASE OF THE ACTIVE INGREDIENT

RELATED APPLICATIONS

This is a National Stage of International Application Number PCT/EP02/06749, filed Jun. 19, 2002.

The present invention relates to modified-release oral pharmaceutical compositions containing one or more active principles solubilised, suspended or embedded in an amphiphilic matrix suitably formulated which, loaded in hydrophilic matrices, provides different release profiles. The compositions of the invention are able to modulate the in vitro and in vivo performances of those drugs which require repeated daily administrations or which have to be carried and released at specific sites of the gastrointestinal tract.

Formulation of drugs in amphiphilic matrix systems, with other surfactants, cyclodextrins and/or polymers and other excipients which are used for obtaining pharmaceutical forms having suitable technological properties, allows to increase and modulate the in vitro dissolution rate and to attain the prompt release of the active ingredient. Furthermore, amphiphilic systems provide homogeneous distribution of active principles having different chemical-physical characteristics (lipophilic and hydrophilic drugs) in the formulations. The amphiphilic matrix, once loaded in hydrophilic matrix systems, which swell upon contact with biological fluids, is able to modulate the homogeneous release of the active ingredient at a constant rate, to provide suitable release kinetics.

The modified-release compositions of the invention may contain active principles belonging to the therapeutical classes of analgesic, anti-inflammatory, antineoplastic, immunomodulating, antihemetic, antidiabetic, cardiovascular, hypnotic, tranquilizing, antihistamine drugs.

TECHNOLOGICAL BACKGROUND

A sustained-, delayed-, extended-, controlled- or anyway modified-release formulation can be prepared according to different known techniques:

Use of inert matrices, in which the main structural component is a highly lipophilic material having poor affinity to biological fluids, which affords some resistance to penetration of said fluids.

Use of hydrophilic matrices, in which the structural component affords a marked resistance to wetting and solubilization in biological fluids, as the system tends to form gels and to gradually swell in time.

Use of bioerodible and/or biodegradable matrices, in which the used polymers and materials gradually undergo metabolic and/or physiological degradation at certain biological sites.

Use of mixed matrices, which comprises the use of inert lipophilic matrices with hydrophilic systems or 3-matrix-systems, i.e. hydrophilic-amphiphilic-lipophilic matrices, where different interactions with different release kinetics take place.

All the above mentioned procedures suffer, however, from some drawbacks and disadvantages.

Inert matrices generally provide non-linear but exponential release kinetics of the active ingredient.

Hydrophilic matrices have at first a straight line dissolution profile then after a certain part of the active ingredient has been released, they deviate from release linearity.

Bioerodible and/or biodegradable matrices require the ideal enzyme and/or biological environment for the constant release of the drug.

Mixed matrices consist of suitably mixed lipophilic and hydrophilic matrices combined or by lipophilic, amphiphilic and hydrophilic matrices. Although being a progress as for modified release, they do not contain materials able to improve and guarantee restricted release of the drug as well as homogeneous absorption in the gastrointestinal tract, after the drug has been released.

When a modified-release formulation of a drug having either topical activity in the gastrointestinal tract or systemic activity is required, the controlled release has to be ensured from the very first moment after the administration. A somewhat homogeneous release range in time is also necessary, while ensuring, after an amount of the active ingredient has been released, the rapid activity of the drug both topically and systemically, thanks to it being present as microemulsion, solubilized or complexed.

DISCLOSURE OF THE INVENTION

This object has been attained according to the present invention, through the combination of a specific amphiphilic matrix, single or complex, suitably formulated and subsequently embedded in superficially hydrophilic matrix. The inventors did not take into consideration lipophilic matrices. Amphiphilic matrices were suitably selected and formulated for balancing any fast onset phase of the amount of drug present at the surface, for homogeneously modulating all the release phases from the system, including the ability for the formulation to be homogeneously absorbed, without losing the effectiveness of the system.

More particularly, the modified-release pharmaceutical compositions of the invention comprise:

1. a matrix consisting of amphiphilic compounds either liquid or with melting point below 60° C., possibly to form eutectic mixture melting at 35-37° C., in which the active ingredient is at least partially soluble and/or dispersed and/or inglobated or granulated with amphiphilic compound previously solubilised or suspended in solvent (preferably water);
2. a surface acting component which is compatible with the amphiphilic matrix and can be homogeneously solubilized and/or dispersed in the amphiphilic matrix;
3. a component based on cyclodextrins and/or polymers which can be dispersed in the surface-activated amphiphilic matrix or can in turn be loaded on the amphiphilic matrix, either surface-activated or not, to obtain a liquid, semisolid or solid form;
4. a hydrophilic matrix in which the complex amphiphilic matrix is dispersed and part of the active ingredient can be dispersed;
5. any other excipients.

DETAILED DISCLOSURE OF THE INVENTION

The compositions of the invention can be obtained with a process which comprises the following steps:

a) adding surfactants to the amphiphilic matrix, to obtain a homogeneous solution or dispersion;
b) solubilizing, suspending, dispersing, totally or partly embedding one or more active principles;
c) adding cyclodextrins and/or polymers, or granulating or dispersing with cyclodextrins and/or polymers;
d) adding a hydrophilic matrix;
e) optionally adding excipients;

f) optionally film-coating with cellulose derivatives or methacrylic polymers.

More particularly, according to the present invention:

In step a) the surface-activated amphiphilic matrix is prepared. First any amphiphilic semisolid excipients or mixtures thereof are melted above 60° C., or solubilised or suspended in solvent (preferably water), to obtain a homogeneous solution and/or dispersion, which becomes again semisolid or solid at room temperature, with eutectic properties at temperatures ranging from 35° C. to 37° C. (body temperature) or able to be used as granulating system. Afterwards, said excipients, which have become liquid upon melting or are already liquid at room temperature, are added with surfactants to obtain a homogeneous dispersion.

In step b), the active ingredient is solubilised, dispersed and/or inglobated in the surface-activated amphiphilic matrix from step a) to obtain a homogeneous solution and/or dispersion and/or granules.

In step c), the system from step (b) is added with different amounts of cyclodextrins and/or polymers until homogeneous dispersion. Alternatively, the system from step (b) can be loaded onto cyclodextrins and/or polymers and/or mixtures thereof to obtain powder, microgranules or granules having good free-flowing and/or tabletting characteristics.

In step d), one or more hydrophilic excipients, which undergo marked swelling in the presence of water (hydrogels), may be added.

In step e), excipients with different functions, to transform liquid or semisolid formulations into solid ones for the preparation of capsules, tablets, granulates, microgranules, minitablets, sachets may be added, such as silica, celluloses, starches, sugars, polyvinyl pyrrolydones, methacrylates, glidants, antiaggregants, lubricants such as magnesium stearate, stearic acid, talc.

Amphiphilic compounds for use in the present invention comprise glycol alkyl ethers such as diethylene glycols monoethyl ether (Transcutol), macrogolglycerids consisting of mixtures of mono-of and triglycerids and of polyethylene glycols and fatty acids (gelucire 44/14; gelucire 50/13) mono and diesters, polyethylene glycols hydroxystearates (Solutol HS 15).

Surfactants for use for use in the present invention comprise phosphatides and lecithins (phosphatidyl cholines, phosphatidyl diethanolamines, sphyngomyelins), anionic and non-ionic emulsifying waxes, sodium lauryl sulfate, sodium dodecyl sulfate, polysorbates, cholic acids, poloxamer, sodium sulfosuccinate, sodium lauryl sarcosinate, dioctylsodium sulfosuccinate.

Cyclodextrins and polymers for use for use in the present invention comprise alpha-beta-gamma cyclodextrins, hydroxyethylcyclodextrins, methylcyclodextrins, hydroxypropylcyclodextrins, sodium croscarmellose (Acdisol), cross-linked polyvinylpyrrolidone, amberlites (IRP 88).

The hydrophilic matrix consists of excipients named hydrogels, which undergo molecular relaxation when passing from the anhydrous to the hydrate state, thus inducing remarkable increase in the system volume, hindrance and weight, due to the coordination of a large number of water molecules by the polar groups in the polymer chain. Examples of hydrogels for use in the invention, comprise substances selected from acrylic or methacrylic polymers or copolymers, alkylvinyl polymers, hydroxyalkyl celluloses, carboxyalkyl celluloses, polysaccharides, alginates, pectins, starches and derivatives, natural and synthetic gums, polycarbophil, chitosans.

According to a general procedure of the invention, an amphiphilic matrix is first is prepared in the form of a mixture soluble or melted at temperatures above 60° C. and/or solubilised and/or dispersed in solvents (preferably water), containing one or more amphiphilic materials, which is added with one or more surfactants. The amount of surfactant usually does not exceed 10% w/w, the optimum amount ranging from 0.1% to 5%.

This mixture may be added with an amount of cyclodextrin or polymer of up to 10%, the optimum amount ranging from 0.1% to 2.5%, to obtain a homogeneous dispersion.

The active ingredient may be dissolved and/or dispersed and/or granulated in this system up to concentrations ranging from 0.1% to 50%, preferably from 0.1% to 4.9%.

Alternatively, the liquid or semisolid amphiphilic matrix may be used as granulating component. Once melted, or solubilised and/or dispersed in solvents (preferably water), this matrix containing part of the surfactants, dextrins, polymers and active ingredient solubilised or dispersed or granulated, can be added to a significant amount of polymers and/or cyclodextrins already containing the remainder of the active ingredient, to obtain a solid composition ready for further formulation with the addition of the hydrophilic matrix or with mixtures of hydrophilic matrices having different viscosity values, in weight ratios typically ranging from 99.5:0.5 to 0.5:99.5 (amphiphilic matrix:hydrophilic matrix), and of suitable adjuvants such as silica, microcrystalline celluloses, starches, lubricants. The cooled semisolid amphiphilic matrix cools, as well as the extrusion and/or granulation, promotes the compacting of the formulation, to obtain a granule or microgranule easy to process. The final pharmaceutical form may be prepared by dry- or wet-granulation with granulating excipients.

The capsules, microgranules and/or tablets can be subjected to conventional coating processes with gastro-soluble films or gastro-protected with cellulose and methacrylic polymers.

The active principles which can be conveniently formulated according to the invention comprise:

1. Antineoplastics and immunomodulators, such as: cyclophosphamide, chlorambucil, melfalan, busulfan, methotrexate, fludarabine, mercaptopurine, thioguanine, fluorouracil, tegafur, etoposide, idarubicin, procarbazine, estramustine, hydroxycarbamide, irinotecan, topotecan, tretinoin, medroxyprogesterone, megestrol, tamoxifen, toremifen, bicalutamide, flutamide, aminoglutetimide, anastrozole, exemestane, letrozole, levamisole, cyclosporin, micofenolate mofetil, tacrolimus, doxorubicin, epirubicin, dacarbazine, paclitaxel, daunorubicin.
2. Detoxicant compounds for cytostatic treatments, such as: calcium folinate, calcium levofolinate, folic acid.
3. Anti-inflammatories, analgesics and antirheumatics, such as: acetaminophen, phenacetin, sodium salicylate, acetametacin, diclofenac, fentiazac, indomethacin, proglumetacin, sulindac, cinnoxicam, meloxicam, piroxicam, tenoxicam, thiaprophenic acid, flurbiprofene, furprofene, ibuprofen, ketoprofen, naproxen, oxaprozin, mefenamic acid, niflunic acid, amtolmetin guacil, nabumetone, nimesulide, etodolac, glucosamine and its salts.
4. Drugs for the treatment of the bone diseases, such as: alendronic acid, clodronic acid, etidronic acid, risedronate.
5. Antitussives, such as: dextromethorphan, codeine phosphate, levodropropizine.
6. Systemic antihistamines, such as: mequitazine, prometazine, cetrizine, oxatomide, acrivastatin, fexofenadine, ketotifene, loratadine, mizolastine, terfenadine.
7. Antiemetics, antinausea, such as: dolasetron, granisetron, ondansetron, tropisetron, proclorperazine.
8. Antipropulsives, such as: loperamide.

9. Oral hypoglycemizining antidiabetics, such as: metformin, chlorpropamide, glybenclamide, glyclazide, glymepiride, glypizide, glyquidone, glysolamide.
10. Cathartics, such as: bisacodil, sodium picosulfate.
11. Antihypertensives, ace-inhibitor, betablocker, antiarhitmic and coronarodilators, such as: captopril, labetalol, atenolol, propafenone isosorbide mono-dinitrate, carvedilol.
12. Calcium antagonists, such as: nifedipine, nicardipine, diltiazem, verapamil.
13. Antiparkinson drugs, such as: pergolide, carbidopa, levodopa.
14. Intestinal anti-inflammatories, such as: olsalazine, 5-aminosalicylic, sulfasalazine, budesonide, ciclesonide, betamethasone, beclomethasone.
15. Anxiolytics as: chlordiazepoxide, oxazepam, medazolam, alprazolam, donazepam, lorazepam.
16. Antiepileptics, such as: valproate, carbamazepine, phenytoin, gabapentin, tiagabine, lamotrigine, topiramate, biperidene, bornaprine, metixene, procyclidine, trihexyphenidyl.
17. Alpha-Blockers, such as: doxazosin, terazosin, urapidil.
18. Diuretics, such as: chlorthalidone, fenquizone, indapamide, metolazone, xipamide, bumetanide, furosemide, piretanide, toresamide, etozolin.
19. Hypolipemizing agents such as: atorvastatin, cerivastatin, fluvastatin, pravastatin, simvastatin, lovastatin.
20. 5HT1 selective antagonists such as: rizatrepan, sumatripan, zolmitripan, pizotifen.
21. Anticholinergic such as: cimetropium bromide, otilonium bromide, prifinium bromide, scopolamine buthylbromide.
22. Lissive: mebeverine, rociverine, trimebutin.
23. Antidepressant such as: paroxetine, fluvoxamine, fluoxetine, sertraline, mirtazapine.
24. Antibiotics such as: cefadroxil, ofloxacin, ciprofloxacin, doxycyclin, erytromycin, cefaclor, ampicillin, cephradine, doxacillin, cefuroxime axetil, amoxicillin, potassium clavulanate, clarithromicin, norfloxacin.
25. Ematological such as: bromeline.

As far as dissolution characteristics are concerned, these formulations, when contacted with water or aqueous fluids, undergo modified, delayed release of the active ingredient which is present in the resulting dispersion, solubilization and/or emulsion of the system. Surfactants, cyclodextrins and polymers present in the amphiphilic structure favor wettability of the system and the homogeneous release in solution of the active principles within restricted ranges, thus promoting the continuous, gradual absorption or the gradual topical release in the gastrointestinal tract.

The following examples illustrate the invention in greater detail.

Example 1

50 g of flutamide are suspended in an kneaded with 45 g of gelucire 44/14 and 5 g of solutol HS 15 suitably melted and kept at a temperature ranging between 55° C. and 65° C.

750 g of flutamide are loaded into a granulator/homogenizer and the hot mixture prepared above is added thereto. The mixture is further granulated with an aqueous solution/suspension containing 5 g of sodium lauryl sulfate and 10 g of betacyclodextrins to obtain a homogeneous granulate. 5 g of crospovidone and 80 g of hydroxypropyl methylcellulose (hydrophilic matrix) are added in succession into the granulator.

The components are mixed to homogeneous dispersion of the matrices, then 100 g of microcrystalline cellulose, 5 g of magnesium stearate, 5 g of talc and 10 g of colloidal silica are added in succession.

The final mixture is tabletted to unitary weight of 1070 mg/tablet, so that 750 mg of active ingredient per single tablet are administered.

The resulting tablets are then film coated with ethylcellulose and plasticizers.

The tablets were subjected to dissolution test in simulated gastric juices and/or intestinal environment, showing the following release profile: after 60 minutes no more than 30%, after 180 minutes no more than 60%, after 5 hours no more than 80%.

Example 2

45 g of gelucire 44/14 are melted and kept at a temperature ranging between 55° C. and 65° C. 5 g of Transcutol are added to gelucire 44/14 under strong stirring for at least 5 minutes. The stirred mixture is added with 5 g of dioctyl sodium sulfosuccinate and 10 g of betacyclodextrins.

75 g of calcium folinate are loaded into a granulator/homogenizer and the hot mixture obtained above is added thereto. The mixture is granulated to homogeneity, then 100 g of hydroxypropyl methylcellulose (hydrophilic matrix) and 50 mg of policarbophil are added in the granulator. The components are mixed to homogeneous dispersion of the matrices, then 210 g of prosolv, 5 g of magnesium stearate and 5 g of colloidal silica are added in succession.

The final mixture is tabletted to unitary weight of 510 mg/tablet, so that 75 mg of active ingredient per single tablet are administered.

The resulting tablets are then film coated with ethylcellulose and plasticizers.

the tablets were subjected to dissolution test in gastric juices and/or in simulated intestinal environment showing the following release profile: after 60 minutes no more than 25%, after 180 minutes no more than 50%, after 5 hours no more than 70%.

Example 3

25 g of 5-FU (Fluorouracil) are suspended and impastati with 15 g of Transcutol and 5 g lecithins. 225 g of 5-FU (5-fluorouracil) are loaded into a granulator/homogenizer, and the mixture prepared above is added thereto. The mixture is further granulated with an aqueous solution containing 50 g polyvinylpyrrolidone to obtain a homogeneous granulate. 150 g of hydroxypropyl methylcellulose (hydrophilic matrix) are added into the granulator. The components are mixed to homogeneous dispersion of the matrices and then 130 g of microcrystalline cellulose, 5 g of magnesium stearate, 5 g of talc are added in succession.

The final mixture is tabletted to unitary weight of 610 mg/tablet so that 250 mg of active ingredient per single tablet are administered.

The resulting tablets are then film coated with cellulose acetophthalate or polymethacrylates and plasticizers to ensure gastric resistance and to prevent gastric release of active ingredient.

The tablets were subjected to dissolution test in gastric juices and/or in simulated intestinal environment showing the following release profile: after 120 minutes in gastric juices 0%, after 60 minutes in enteric juice no more than 25%, after 180 minutes no more than 50%, after 6 hours no more than 80%.

Example 4

900 g of gabapentin are loaded into a granulator/homogenizer, and a molten mixture containing a suspension of 50 g of gelucire 50/14, 5 g of Solutol HS 15 and 5 g of Acdisol is added thereto. The mixture is further granulated with an aqueous solution/suspension containing 5 g of sodium lauryl sulfate and 25 g of betacyclodextrins to obtain a homogeneous granulate. 110 g of hydroxypropyl methylcellulose (hydrophilic matrix) are added in the granulator. The components are mixed to homogeneous dispersion of the matrices, then 90 g of Prosolv, 5 g of magnesium stearate, 5 g of talc and 10 g of colloidal silica are added in succession.

The final mixture is tabletted to unitary weight of 1210 mg/tablet so that 900 mg of active ingredient per single tablet are administered.

The resulting tablets are then film coated with ethylcellulose and plasticizers.

The tablets were subjected to dissolution test in gastric juices and/or in simulated intestinal environment showing the following release profile: after 60 minutes no more than 30%, after 180 minutes no more than 60%, after 5 hours no more than 80%.

Example 5

850 g of metformin are loaded into a granulator/homogenizer and a molten mixture containing a suspension with 50 g of gelucire 44/14, 5 g of Sodium lauryl sulfate and 5 g of Acdisol is added thereto. The mixture is further granulated with an aqueous solution containing 50 g of polyvinylpyrrolidone to obtain a homogeneous granulate. 100 g of hydroxypropyl methylcellulose (hydrophilic matrix), and 50 g of policarbophyl are added in succession in the same granulator. The components are mixed to homogeneous dispersion of the matrices, then 90 g of Prosolv, 5 g of magnesium stearate, 5 g of colloidal silica are added in succession.

The final mixture is tabletted to unitary weight of 1200 mg/tablet so that 850 mg of active ingredient per single tablet are administered.

The resulting tablets are then film coated with ethylcellulose and plasticizers.

The tablets were subjected to dissolution test in gastric juices and/or in simulated intestinal environment showing the following release profile: after 60 minutes no more than 25%, after 180 minutes no more than 55%, after 6 hours no more than 80%.

As far as Metformin, the following pictures in graphics 1 and 2 showed the pharmacokinetic results after the administration in 6 healthy volunteers of modified release tablet vs originator plain form. As well as indicated in the raw data available, there are significant differences into the MRT and T max data.

Example 6

15 g of gelucire 44/14 are melted and kept at a temperature ranging from 55° C. and 65° C. 1.5 g of Solutol HS 15 are added thereto under strong stirring for at least 5 minutes. The stirred mixture is added with 1.5 g of dioctyl sodium sulfosuccinate and 1 g of betacyclodextrins.

10 g of Glipizide are loaded into a granulator/homogenizer and the hot mixture obtained above is added thereto. The mixture is granulated to obtain a homogeneous mixture. 50 g of hydroxypropyl methylcellulose, 10 g of policarbophyl and 17 g of betacyclodextrins granulator are added into the granulator. The components are mixed to homogeneous dispersion of the matrices, then 90 g of microcrystalline cellulose, 50 g of Prosolv, 5 g of magnesium stearate 5 g of talc and 10 g of colloidal silica are added in succession.

The final mixture is tabletted to unitary weight of 270 mg/tablet so that 15 mg of active ingredient per single tablet are administered.

The resulting tablets are then film coated with ethylcellulose and plasticizers.

The tablets were subjected to dissolution test in gastric juices and/or in simulated intestinal environment showing the following release profile: after 60 minutes no more than 25%, after 180 minutes no more than 50%, after 5 hours no more than 70%, after 6 hours no more than 80%.

Example 7

50 g of gelucire 50/13 and 10 g of solutol HS 15 are suitably melted and kept at a temperature of about 60° C.

500 g of mesalamine are loaded into a granulator/homogenizer and the hot mixture prepared above is added thereto. The mixture is further granulated with an aqueous solution/suspension containing 5 g of sodium lauryl sulfate and 10 g of hydroxypropylmethylcellulose low viscosity to obtain an homogeneous granulate.

150 g of hydroxypropylmethylcellulose high viscosity are added into the granulator. The components are mixed to the homogeneous dispersion of the matrix; than 100 g of microcrystalline cellulose, 5 g of magnesium stearate, 5 g of colloidal silica are added.

The final mixture is tabletted to unitary weight of 835 mg per tablet, so that 500 mg of active are administered.

The resulting tablets are film coated with 60 mg of polymetacrilates mixture (2 L/1 S) to ensure gastric resistance until pH 6.4.

The tablets were subjected to dissolution test at different pH showing the following release profile:

After 120 minutes at pH 1.2, 0%; after 60 minutes at pH 6.4 less than 5%; at pH 7.2 after 2 hours no more than 25%; after 4 hours no more than 50%, after 6 hours no more than 80%.

The invention claimed is:

1. Oral controlled-release pharmaceutical composition, consisting essentially of:
   a) an active ingredient;
   b) a macrogolglyceride matrix, optionally in combination with diethylene glycol monoethyl ether or polyethylene glycol hydroxystearate, forming a eutectic mixture melting at 35-37° C., in which matrix the active ingredient is at least partially soluble and/or dispersed and/or embedded or granulated with said macrogolglycerides previously solubilised or suspended in solvent;
   c) a surface-acting component selected from lecithins, dioctyl sodium sulfosuccinate, sodium lauryl sulfate, sodium sulfosuccinate, and sodium dodecyl sulfate;
   d) cyclodextrins or a polymer selected from croscarmellose sodium or cross-linked polyvinylpyrrolidone dispersed in or loaded on said surface-activated macrogolglyceride matrix, to obtain a liquid, semisolid or solid form;
   e) a hydrophilic matrix in the form of a hydrogel consisting of cellulose derivatives, wherein the macrogolglyceride matrix is dispersed within the hydrophilic matrix; and
   f) optional excipients.

2. Composition as claimed in claim 1 wherein the cyclodextrins are alpha-beta-gamma cyclodextrins, hydroxyethylcyclodextrins, methylcyclodextrins, or hydroxypropylcyclodextrins.

3. Composition as claimed in claim 1, wherein the cellulose derivatives in the hydrophilic matrix are hydroxypropylmethylcellulose.

4. Composition as claimed in claim 1, wherein the active ingredient is in part present in the macrogolglyceride matrix and in part loaded on the cyclodextrins or polymer, in the form of minitablets, granules or microgranules.

5. Oral controlled-release pharmaceutical composition, consisting essentially of:
   a) an active ingredient;
   b) a macrogolglyceride matrix, optionally in combination with diethylene glycol monoethyl ether or polyethylene glycol hydroxystearate, forming a eutectic mixture melting at 35-37° C., in which matrix the active ingredient is at least partially soluble and/or dispersed and/or embedded or granulated with said macrogolglycerides previously solubilised or suspended in solvent;
   c) a surface-acting component selected from lecithins, dioctyl sodium sulfosuccinate, sodium lauryl sulfate, sodium sulfosuccinate, and sodium dodecyl sulfate;
   d) cyclodextrins or a polymer selected from croscarmellose sodium or cross-linked polyvinylpyrrolidone dispersed in or loaded on said surface-activated macrogolglyceride matrix, to obtain a liquid, semisolid or solid form;
   e) a hydrophilic matrix in the form of a hydrogel consisting of cellulose derivatives, wherein the macrogolglyceride matrix is dispersed within the hydrophilic matrix;
   f) optional excipients; and
   g) gastro-soluble or gastro-resistant coating of cellulose derivatives or methacrylic acid polymers.

6. Composition according to claim 1, wherein the active ingredient belongs to therapeutical categories selected from antineoplastics and immunomodulators, detoxicant compounds for cytostatic treatments, anti-inflammatories, analgesics and antirheumatics, drugs for the treatment of bone diseases, antitussives, systemic antihistamines, antiemetics, antinausea agents, antipropulsives, oral hypoglycemizing antidiabetics, cathartics, antihypertensives, ace-inhibitors, betablockers and coronarodilators, calcium antagonists, antiparkinson drugs, intestinal anti-inflammatories, anxiolytics, antiepileptics, alpha-blockers, diuretics, hypolipemizing agents, 5HT1 selective antagonists, anticholinergics, lissives, antidepressants, and antibiotics.

7. Composition as claimed in claim 1, wherein the active ingredient is selected from etoposide, calcium folinate, methotrexate, cyclophosphamide, procarbazine, fluorouracil, idarubicin, glypizide, glybenclamide, flutamide, nimesulide, piroxicam, ketoprofen, ibuprofen, gabapentin, 5-aminosalicylic, budesonide, metformin, and mesalamine.

8. Composition as claimed in claim 1 wherein part of the active ingredient is dispersed in said hydrophilic matrix.

9. The composition as claimed in claim 1, wherein the solvent is water.

* * * * *